(12) United States Patent
Popescu

(10) Patent No.: US 10,816,618 B2
(45) Date of Patent: Oct. 27, 2020

(54) POSITIONING OF A MAGNETIC RESONANCE BODY COIL

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 227 days.

(21) Appl. No.: 15/988,418

(22) Filed: May 24, 2018

(65) Prior Publication Data

US 2018/0348314 A1 Dec. 6, 2018

(30) Foreign Application Priority Data

Jun. 2, 2017 (EP) ..................... 17174253

(51) Int. Cl.
*G01R 33/34* (2006.01)
*A61B 5/055* (2006.01)
(Continued)

(52) U.S. Cl.
CPC .............. *G01R 33/34* (2013.01); *A61B 5/055* (2013.01); *G01R 15/22* (2013.01); *G01R 33/28* (2013.01); *H04N 5/33* (2013.01)

(58) Field of Classification Search
CPC ........ G01R 33/34; G01R 33/28; G01R 33/22; A61B 5/055; H04N 5/33
See application file for complete search history.

(56) References Cited

U.S. PATENT DOCUMENTS 6,317,619 B1 * 11/2001 Boernert .............. G01R 33/341
324/307
6,608,688 B1 8/2003 Faul et al.
(Continued)

FOREIGN PATENT DOCUMENTS

DE 102009005188 A1 7/2010
DE 102012209190 A1 12/2013
(Continued)

OTHER PUBLICATIONS

European Office Action for European Patent Application No. 17174253.9-1115, dated Oct. 1, 2018.
(Continued)

*Primary Examiner* — Dixomara Vargas
(74) *Attorney, Agent, or Firm* — Lempia Summerfield Katz LLC

(57) ABSTRACT

A magnetic resonance (MR) body coil is provided with a supporting surface for support on an object to be examined and an outer side remote from the support side, wherein at least one light source is fastened to the outer side at a predefined position. A magnetic resonance system has at least one MR body coil and an image acquisition device for acquiring light, which may be radiated by the at least one light source of the at least one MR body coil. A method is used for operating a MR body coil, wherein at least one light source radiates light for positioning the MR body coil. A further method is used for positioning a MR body coil on an object to be examined, wherein at least one light source fastened to a MR body coil radiates light, the light is acquired by an image acquisition device, which includes at least one camera, and at least one position of the at least one light source is determined by the acquisition.

20 Claims, 2 Drawing Sheets

(51) Int. Cl.
    *G01R 33/28*     (2006.01)
    *G01R 15/22*     (2006.01)
    *H04N 5/33*     (2006.01)

(56) References Cited

U.S. PATENT DOCUMENTS

| | | | |
|---|---|---|---|
| 7,180,294 B2 | 2/2007 | Kohlmuller | |
| 8,212,558 B2 | 7/2012 | Mueller | |
| 8,548,560 B2 * | 10/2013 | Saes | G01R 33/3621 |
| | | | 600/407 |
| 10,001,534 B2 * | 6/2018 | Okamoto | G01R 33/3692 |
| 10,448,003 B2 * | 10/2019 | Grafenberg | H04N 13/282 |
| 2005/0254714 A1 | 11/2005 | Ramakrishna | |
| 2007/0182409 A1 * | 8/2007 | Varjo | G01R 33/3415 |
| | | | 324/304 |
| 2010/0156421 A1 * | 6/2010 | Sukkau | G01R 33/3415 |
| | | | 324/318 |
| 2010/0182005 A1 | 7/2010 | Biber | |
| 2012/0046521 A1 * | 2/2012 | Hunter | A61B 5/065 |
| | | | 600/104 |
| 2012/0059220 A1 * | 3/2012 | Holsing | A61B 5/418 |
| | | | 600/109 |
| 2012/0059248 A1 * | 3/2012 | Holsing | A61B 1/00094 |
| | | | 600/424 |
| 2013/0165767 A1 | 6/2013 | Darrow et al. | |
| 2013/0342350 A1 | 12/2013 | Popescu | |
| 2013/0342851 A1 | 12/2013 | Dresel et al. | |
| 2014/0062485 A1 * | 3/2014 | Okamoto | G01R 33/24 |
| | | | 324/322 |
| 2014/0070811 A1 | 3/2014 | Tomiha et al. | |
| 2015/0281680 A1 * | 10/2015 | Grafenberg | H04N 13/156 |
| | | | 348/50 |
| 2015/0287318 A1 | 10/2015 | Nair et al. | |
| 2016/0298796 A1 * | 10/2016 | Anton | F16L 19/061 |
| 2017/0020409 A1 | 1/2017 | Hengerer et al. | |
| 2017/0269176 A1 * | 9/2017 | Weiss | A61B 5/01 |

FOREIGN PATENT DOCUMENTS

| | | |
|---|---|---|
| DE | 102015213935 A1 | 1/2017 |
| EP | 2927854 A1 | 10/2015 |
| WO | WO9952094 A1 | 10/1999 |
| WO | WO2015169655 A1 | 11/2015 |

OTHER PUBLICATIONS

Ettinger, Gil J., et al. "Experimentation with a transcranial magnetic stimulation system for functional brain mapping." Medical image analysis 2.2 (1998): 133-142.
Weiduschat, Nora, et al. "Localizing Broca's area for transcranial magnetic stimulation: comparison of surface distance measurements and stereotaxic positioning." Brain Stimulation: Basic, Translational, and Clinical Research in Neuromodulation 2.2 (2009): 93-102.
European Search Report for corresponding Application No. 17174253.9-1657, dated Nov. 18, 2018.

* cited by examiner

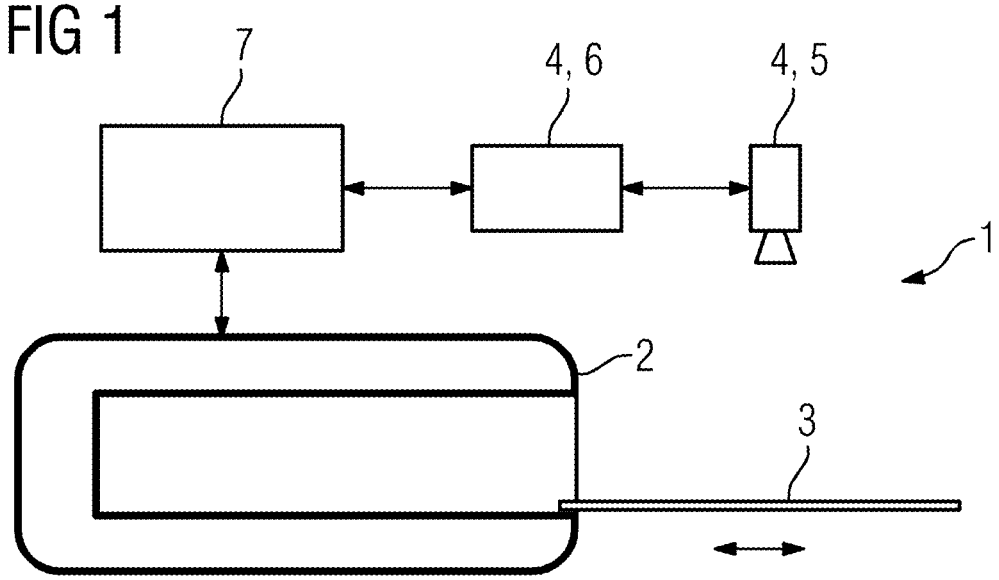
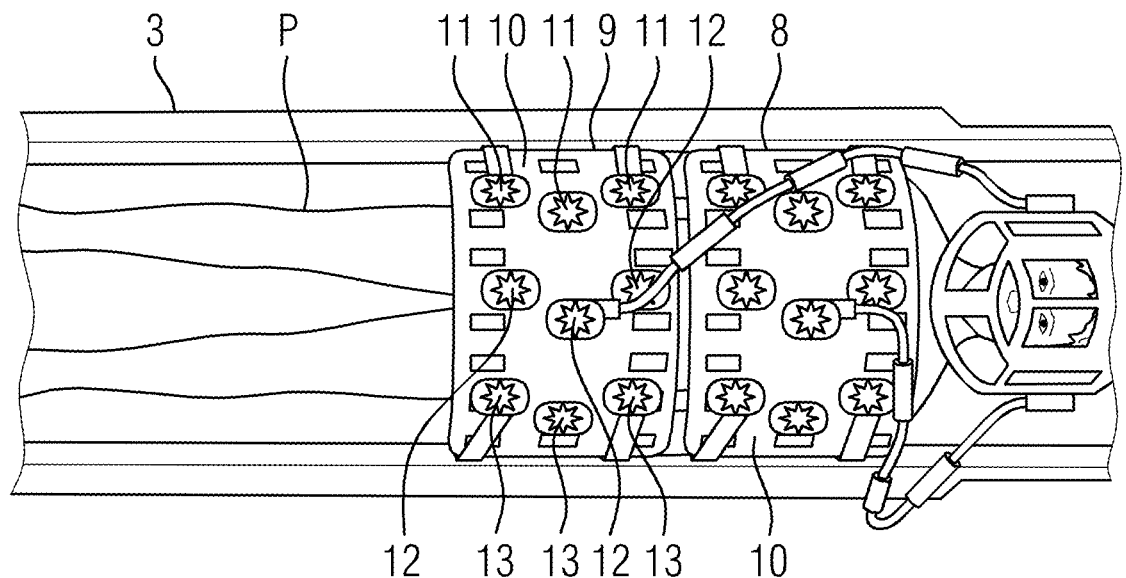

POSITIONING OF A MAGNETIC RESONANCE BODY COIL

The application claims the benefit of European Patent Application No. EP 17174253.9, filed Jun. 2, 2017, which is hereby incorporated by reference in its entirety.

TECHNICAL FIELD

The disclosure relates to a magnetic resonance (MR) body coil for use in magnetic resonance imaging. The disclosure also relates to a magnetic resonance (MR) imaging system, which has a MR body coil and an image acquisition device. The disclosure also relates to a method for operating a MR body coil. The disclosure relates, moreover, to a method for positioning a MR body coil on an object to be examined, wherein an image of the MR body coil is acquired by a camera and a position of the body coil is determined by the acquisition.

BACKGROUND

There is a need in the technical field of medical imaging diagnostics, (e.g., magnetic resonance imaging), for autonomously operating imaging equipment in order to prevent or rule out operating errors and/or in order to also be able to guide less experienced operators through the imaging sequence while strictly adhering to quality guidelines. For efficient operation of a magnetic resonance acquisition device (e.g., a "MR scanner"), there is therefore a requirement for exact positioning of receive coils, (e.g., local coils), on the body of a patient to be examined (e.g., "body coils") in respect of the anatomy of the body as well as in respect of exact positioning of the body regions in an area with the greatest homogeneity of the magnetic field.

Until now, correct positioning of the body coils has been the responsibility of the operator. Incorrect positioning of the body coils may occur due to human errors, such as stress, tiredness, etc., and/or owing to poor training, etc. Incorrect positioning leads to impairment of scanning and image quality of the MR scan and/or to a need to correct the position of the receive coils and to subsequently repeat the MR scan. A patient potentially has to be rescheduled in order to repeat the MR scan.

Methods for positioning MR coils and/or patients are described, for example, in U.S. Pat. No. 8,212,558 B2 and U.S. Pat. No. 7,180,294 B2. Correct positioning of the patient, or his organs to be examined, in the MR scanner is based on the skills of the operator. The operator may be capable of identifying and selecting visible anatomical features of the body and to then use a laser positioning system to move an examination table such that the organs to be examined are located in the magnetic isocenter of the MR scanner.

U.S. Patent Application Publication No. 2013/0342350 A1 discloses a method, which is based on a video camera and image processing algorithms in order to automatically detect positions and orientations of body coils in relation to a patient's anatomy and to supply acoustic and visual feedback to an operator in order to prevent and correct positioning errors before a scan is performed or even before the examination table in is pushed into a recording space of the MR scanner. The accuracy of this method depends on the reliability of the image processing algorithms. This is disadvantageous, for example, for the case where the body of a patient is covered by a blanket in order to avoid body temperature reduction. In this case and if the patient preparation, including placement of the coils and relocation of the blanket outside of a field of view of the video camera, has been carried out, subsequent acquisition of the coil position is made difficult.

SUMMARY AND DESCRIPTION

The scope of the present disclosure is defined solely by the appended claims and is not affected to any degree by the statements within this summary. The present embodiments may obviate one or more of the drawbacks or limitations in the related art.

It is the object of the present disclosure to overcome the drawbacks of the prior art at least partially and, in particular, to provide a possibility for being able to detect a position and/or an orientation of MR body coils better.

The object is achieved by a MR body coil, to which at least one light source is fastened at a predefined position.

A MR body coil may refer to a local coil and/or surface coil and not, for instance, a body coil, which is conventionally permanently fitted in a MR scanner.

This body coil has the advantage that an illuminating light source of an image recognition system, in particular of a (e.g., video) camera, may be seen particularly clearly. As a result, the position of the light source and the corresponding position of the body coil may in turn be determined particularly accurately. The light radiated by the light source may also radiate or be visible through a patient's blanket, so sufficiently accurate determination of the position and optionally an orientation of the body coil by image processing is also enabled for a covered patient.

The MR body coil may be provided with a supporting surface for support on an object to be examined and an outer side remote from the support side, wherein at least one light source is fastened to the outer side at a predefined position. The outer side may also include an edge of the body coil.

In one embodiment, the at least one light source includes at least one light-emitting diode. The use of light-emitting diodes (LEDs) is advantageous because the LEDs are very long lasting, have a compact construction, shine very brightly, and demonstrate a sharp spectral spectrum.

In another embodiment, the at least one light source has a plurality of light sources disposed in a predefined arrangement. This embodiment has the advantage that an orientation of the body coil may also be detected through image processing by way of the arrangement. The orientation may include a rotary position and optionally also an angle of inclination of the body coil. Therefore, a rotation and optionally tilting of the body coil with respect to a desired position may be determined in addition to a displacement. The desired position may be defined in relation to the patient and/or in relation to an examination table. Additionally, or alternatively, with flexible body coils, the degree of bending thereof may also be determined by this embodiment.

The orientation may also be quantitatively determined.

In a further embodiment, at least two light sources radiate light of a different spectral composition, (e.g., a different color). This has the advantage that a position and orientation of the body coil may be accurately detected through image processing.

In yet a further embodiment, the at least one light source is an infrared (IR) light source. The infrared light source has the advantage that, owing to lower scattering losses, the infrared radiation radiated thereby may penetrate obstacles, such as (for example wool or material) blanket better than visible light. In particular, a wool blanket may maintain a body temperature effectively by preventing heat loss owing to air convection, whereas it is highly penetrable to infrared radiation.

The infrared light source may radiate only infrared radiation and no visible light. A light source radiating visible light may also radiate IR light or alternatively radiate only visible light.

The infrared radiation radiated by the infrared light source may be near infrared (NIR) light, middle infrared (MIR) light, and/or far infrared (FIR) light.

It is possible for the plurality of light sources to include a combination of light sources, which radiate visible light, and of light sources, which radiate only IR radiation.

In certain embodiments, the at least one light source may be operated to flash in a coded manner. This advantageously enables identification of the light source using its blink code. This is particularly advantageous if identification of a light source is not made using its color, specifically in conjunction with infrared light sources. Use of a blink code or coded flashing may be used as an alternative or in addition to color coding.

A plurality of light sources may be operated in groups to flash in a coded manner with the same blink code. In addition, or in the alternative, light sources with an individual blink code may be operated to flash in a coded manner. The individual coding has the advantage that each light source and its position on the body coil may be individually identified.

The blink code may be a binary code. The blink code may be a Morse code.

A blink rate or blink frequency of the blink code may be chosen such that it may be detected by an image acquisition device. For this purpose, the blink rate may be noticeably shorter than the image acquisition rate, e.g., a maximum of half as much as the image acquisition rate in order to satisfy the Nyquist-Shannon sampling theorem. In one example, the blink rate is at least five times shorter than the image acquisition rate. If, for example, a camera takes images at an image acquisition rate of 25 to 30 images per second (fps), the light source advantageously flashes a maximum of five times per second.

In one embodiment, the at least one light source may be operated to flash in a coded manner for data transfer. This has the advantage that information (e.g., going beyond the identification of the light source) may also be transferred from the body coil to an image acquisition device. Such information may be status information about a state of the body coil, such as a status information or error information, etc. The error information may include one or more error code(s), which correspond, for example, to cases of error in which electronic modules of the body coil are defective. This is particularly advantageous if the body coil is a wirelessly communicating body coil and the wireless communication with the MR scanner is interrupted, for example, owing to external interference or owing to a fault or failure in the electronics of the body coil.

The at least one light source may be supplied with current by way of a coil connection of the body coil. The at least one light source may be supplied with current individually or in groups by a respective driver.

The object is also achieved by a MR system, having a MR body coil (as disclosed above) and an image acquisition device for acquiring light, which may be radiated by the at least one light source of the MR body coil. The MR system may be designed analogously to the body coil and produce the same advantages.

The image acquisition device may be a component of the MR scanner or be a stand-alone device. In particular, if the image acquisition device is a stand-alone device, the image acquisition may also be operated independently of the MR scanner. If the image acquisition device is integrated in the MR scanner, it may be operated before insertion of a patient into the recording space of the MR scanner.

It certain embodiments, an evaluation device for evaluation of the images acquired with the image acquisition device is connected to the image acquisition device or is integrated in the image acquisition device. The evaluation device may determine the position and optionally orientation and/or bend in the body coil using the acquired scans or images, in particular, against respective desired values. In particular, for the case where the at least one light source has a plurality of light sources disposed in a predefined arrangement, this may be carried out by pattern recognition.

The image acquisition device may have at least one camera and a depth sensor. This embodiment enables particularly accurate determination of a position, (e.g., three-dimensional position), and orientation of the light sources. This is particularly advantageous in the case of highly contoured body coils. Particularly accurate determination of a bend in the body is also enabled thereby.

The depth sensor or measured values thereof may be used to limit a search or acquisition region for light sources, in particular, infrared light sources. This is advantageous, for example, in order to suppress or avoid detection of interfering sources, (e.g., light beams reflected by a floor).

In an embodiment, the image acquisition device has a first camera, which is sensitive to a visible light spectrum, and a second camera, which is sensitive to an infrared spectrum. This facilitates the detection of light sources considerably, in particular of light sources, which are covered by a material or wool blanket. Detection may be improved by comparison or combination of results of image recognition in the visible light spectrum with results of image recognition in the IR spectrum.

The two cameras or their functions may also be integrated in a single, multi-spectrally sensitive camera.

The two cameras and the depth sensor may be integrated in a single sensor unit.

The object is also achieved by a method for operating a MR body coil (in particular with a supporting surface for support on an object to be examined and an outer side remote from the support side), in which method at least one light source (e.g., fastened to the outer side) radiates light for positioning the MR body coil. The method may be configured analogously to the MR body coil and has the same advantages.

The object is also achieved by a method for positioning a MR body coil on an object to be examined, in which at least one light source fastened to a MR body coil radiates light, the light is recorded by a camera, and at least one position of the at least one light source is determined by the image recorded by the camera. The method may be configured analogously to the body coil and to the MR system and has the same advantages.

The fact that at least one position of the at least one light source is determined, may include that only the position is determined or may include that the position and at least one further position property of the body coil, such as its orientation (for example, an angle of rotation and/or an angle of inclination) and/or its bend are determined.

In an embodiment, a deviation of at least the determined position from a desired value or desired range is determined. It may therefore advantageously be determined whether the body coil is at a suitable or intended position and optionally in a correct orientation and/or bend for a subsequent MR scan.

In a further embodiment, if the deviation from the desired value exceeds a predefined threshold value, information is output to an operator. The operator may correct the position and/or orientation of the body coil using the information. The information may be acoustic or visual information. The visual information may include information displayed on a screen and correction directions and/or correction lengths.

The method may also be used to transfer status information of the body coil to the image acquisition device by light signals radiated by at least one light source. The MR system may be controlled by the status information, for example a MR device may be switched off if the status information indicates a body coil fault.

BRIEF DESCRIPTION OF THE DRAWINGS

The properties, features, and advantages described above and the manner in which they are achieved will become clearer and more comprehensible in conjunction with the following schematic description of exemplary embodiments, which are illustrated in more detail in connection with the drawings. For the sake of clarity, identical elements or those having the same effect are provided with identical reference numerals.

FIG. 1 depicts a sectional diagram in a side view an exemplary MR device 1.

FIG. 2 depicts in a plan view an example of an examination table with a patient, on which two MR body coils are placed.

DETAILED DESCRIPTION

Figure 3:
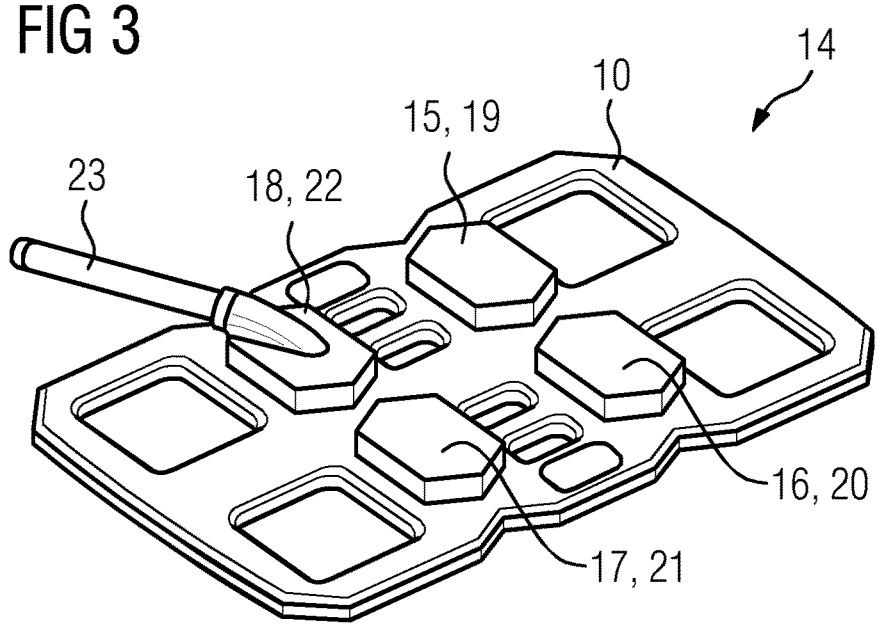
FIG. 3 depicts in an oblique view a further exemplary MR body coil.

FIG. 1 depicts a magnetic resonance (MR) device 1, having a MR scanner 2 with an examination table 3 and with an image acquisition device 4. The image acquisition device 4 has a sensor 5 whose field of view is directed from above onto an examination table 3 that has been pulled out. The image acquisition device 4 also has an image evaluation device 6 coupled to the sensor 5. The image evaluation device 6 may in turn be coupled to a controller 7 of the MR device 1.

The sensor 5 may be a RGB video camera or may have a sensor with a RGB video camera, an IR camera, and/or a depth sensor (not shown).

FIG. 2 depicts in a plan view the examination table 3. Lying on the examination table 3 is a patient P, on which two identical MR body coils 8, 9 are placed with a respective supporting surface (not shown). Fastened to an outer side 10 remote from the support side are in each case per MR body coil 8, 9 nine light sources in the form of LEDs 11, 12, 13 at a strictly predefined position in each case and therewith also in a predefined arrangement to each other. The LEDs 11 to 13 may be components of respective LED modules. The LED modules may also have a driver, a shield, etc. The LED modules may correspond to the electronic modules, for example, if at least one LED has been added to the electronic modules.

The LEDs 11 to 13 are arranged in three parallel rows each with three LEDs 11, 12 and 13, which are provided here to be oriented along a longitudinal extension of the patient P. The middle one of the LEDs 11 to 13 in each case is laterally offset in the rows. The LEDs 11 to 13 radiate light of a different color. The LEDs 11 may radiate red light, the LEDs 12 may radiate green light, and the LEDs 13 may radiate blue or yellow light. In other words, the rows may radiate light of a different color. Alternatively, for example, all LEDs may also radiate light of a different color.

The camera 5 is configured to detect the light radiated by the LEDs 11 to 13, in particular, in an image. The at least one recorded image may be evaluated by the image evaluation device 6. If the sensor 5 has a depth sensor, then this may also be used for image evaluation.

As a result of image evaluation, the positions of the LEDs 11 to 13 and therewith also of the MR body coils 8, 9 as well as optionally their orientation and optionally their bend may be determined, (e.g., in relation to respective desired values). These deviations may be displayed on a monitor by way of the controller 7 (not shown). As a result, an operator watching the monitor (not shown) may adjust the positions, etc. of the MR body coils 8, 9 until the positions, etc., lie within the desired values and are therefore correctly positioned.

In addition, the LEDs 11 to 13 may be operated to flash in a coded manner, for example, in that they flash with an individual Morse code. This further improves identification of the LEDs 11 to 13. In particular, LEDs 11, 12, or 13 of the same color may also be individually identified. Alternatively, LEDs 11, 12, or 13 of the same color may flash by the same code.

Additionally, or alternatively to the LEDs 11 to 13, IR LEDs may be present on the MR body coils 8, 9 and may be detected by the sensor 5. In one variant, identical IR LEDs may be used instead of the LEDs 11 to 13. To be able to identify the IR LEDs in groups or individually, they are operated to flash in a coded manner accordingly.

The sensor 5 may record images at an image acquisition rate von 25 to 30 fps, while the blink rate is at 5 Hz.

It is also possible to operate at least one of the LEDs 11 to 13 or at least one of the IR LEDs to flash in a coded manner for data transfer.

FIG. 3 depicts in an oblique view a further MR body coil 14. The MR body coil 14 has at its outer side four LED modules 15 to 18, which each have at least one LED 19 to 22 and a driver (not shown). The LED module 18 has an electrical connection 23, by which the LED modules 15 to 18 may be supplied with current. The LED modules 15 to 18 may also have a shield for protection against the magnetic field generated in the MR scanner 2.

The LEDs 19 to 22 may radiate light of a different color and/or flash with a different code to enable their individual identification. In particular, if the LEDs 19 to 22 are IR LEDs, they may flash with a different code.

Figure 4:
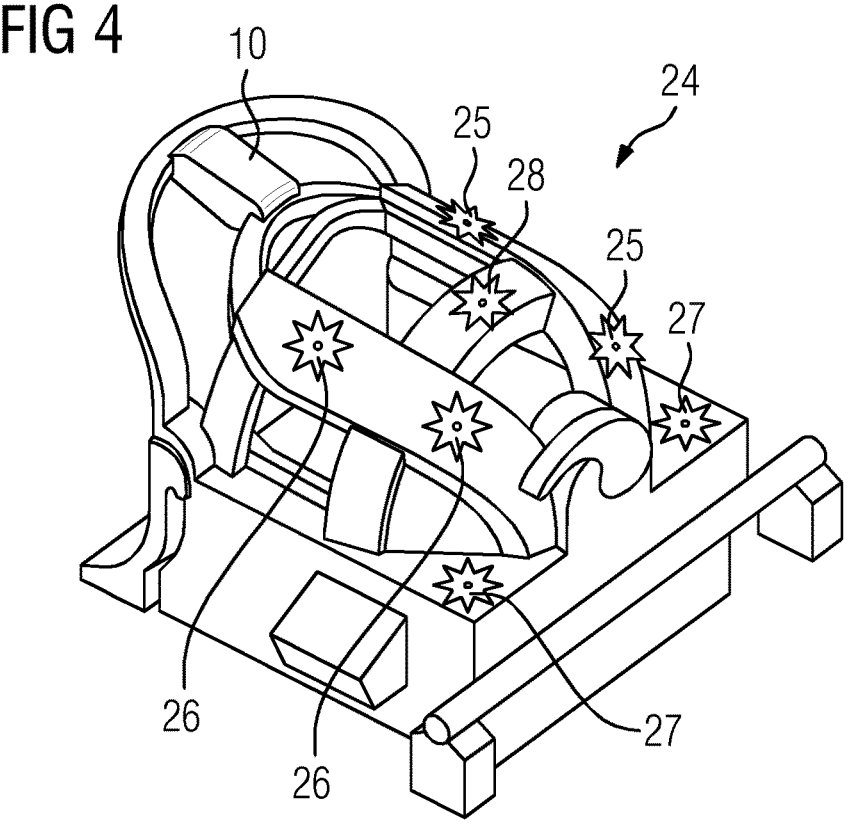
FIG. 4 depicts in an oblique view yet a further exemplary MR body coil.

FIG. 4 depicts in an oblique view yet a further MR body coil 24. This MR body coil 24 is provided for recording a head of the patient P and may also be called a head coil. LEDs 25 to 28 are present at the outer side 10 of the MR body coil 24. In pairs, the LEDs 25 to 27 radiate light of the same color and/or with the same blink code, with the color and/or the blink code being different for different pairs. A central LED 28 radiates light of a different color again and/or with a different blink code again.

In general, "a", "an", etc. may be taken to mean a singular or a plurality, in particular within the meaning of "at least one" or "one or more" etc., as long as this is not expressly ruled out, for example by the expression "exactly one", etc.

A numerical figure may also include exactly the given number as well as a conventional tolerance range as long as this is not expressly ruled out.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance (MR) body coil comprising:
a support side having a supporting surface configured to be positioned on an object to be examined;
an outer side remote from the support side; and
at least one light source fastened to the outer side at a predefined position,
wherein each light source of the at least one light source is configured to flash light in a coded manner to provide a blink code, and
wherein the blink code of each light source is configured to be detected by an image acquisition device of a MR device.

2. The MR body coil of claim 1, wherein the at least one light source comprises at least one light-emitting diode.

3. The MR body coil of claim 1, wherein the at least one light source comprises a plurality of light sources disposed in a predefined arrangement.

4. The MR body coil of claim 3, wherein at least two light sources of the plurality of light sources radiate light of a different spectral composition.

5. The MR body coil of claim 4, wherein the different spectral composition comprises different colors.

6. The MR body coil of claim 1, wherein the at least one light source is an infrared light source.

7. The MR body coil of claim 1, wherein each light source of the at least one light source is configured to flash light in the coded manner for data transfer.

8. The MR body coil of claim 1, wherein a blink rate of each light source of the at least one light source is at least five times slower than an image acquisition rate of the MR device.

9. The MR body coil of claim 1, wherein the blink code is configured to provide status information regarding whether the MR body coil is defective.

10. A magnetic resonance (MR) system comprising:
a MR body coil comprising:
a support side having a supporting surface configured to be positioned on an object to be examined;
an outer side remote from the support side; and
at least one light source fastened to the outer side at a predefined position, wherein each light source of the at least one light source is configured to flash light in a coded manner to provide a blink code; and
an image acquisition device configured to detect each blink code from each light source of the at least one light source.

11. The MR system of claim 10, wherein the image acquisition device comprises at least one camera and a depth sensor.

12. The MR system of claim 11, wherein the at least one camera comprises a first camera sensitive to a visible light spectrum and a second camera sensitive to an infrared spectrum.

13. The MR system of claim 10, wherein the image acquisition device comprises a first camera sensitive to a visible light spectrum and a second camera sensitive to an infrared spectrum.

14. The MR system of claim 10, wherein the blink code is configured to provide status information regarding whether the MR body coil is defective.

15. A method for operating a magnetic resonance (MR) body coil, the method comprising:
providing the MR body coil, the MR body coil comprising: a support side having a supporting surface for support on an object to be examined, an outer side remote from the support side, and at least one light source fastened to the outer side at a predefined position; and
radiating light, by the at least one light source of the MR body coil, for positioning the MR body coil using the radiated light,
wherein each light source of the at least one light source flashes light in a coded manner to provide a blink code, and
wherein the blink code of each light source is configured to be detected by an image acquisition device of a MR device.

16. The method of claim 15, wherein each light source of the at least one light source flashes light in the coded manner for data transfer.

17. The method of claim 15, wherein each light source of the at least one light source flashes a maximum of five times per second.

18. A method for (MR) operating a magnetic resonance (MR) system, the method comprising:
radiating light by at least one light source fastened to a MR body coil of the MR system;
acquiring the radiated light by at least one camera of an image acquisition device of the MR system;
determining, by the image acquisition device, at least one position of the at least one light source by the acquisition acquired radiated light;
determining, by the image acquisition device, a deviation of the at least one determined position from a desired value or desired range; and
outputting, by the MR system, information when the deviation from the desired value exceeds a predefined threshold value.

19. The method of claim 18, wherein the information is output to an operator.

20. The method of claim 18, wherein the image acquisition device comprises a depth sensor, which limits an acquisition region of the at least one camera to the acquisition of the radiated light of the at least one light source.

* * * * *